United States Patent
Ingmanson et al.

(10) Patent No.: US 9,622,745 B2
(45) Date of Patent: Apr. 18, 2017

(54) STAPLE LINE REINFORCEMENT FOR ANVIL AND CARTRIDGE

(71) Applicant: Covidien LP, Mansfield, MA (US)

(72) Inventors: Michael D. Ingmanson, Stratford, CT (US); Sachin Shah, Milford, CT (US); Joseph McNellis, Bristol, CT (US)

(73) Assignee: Covidien LP, Mansfield, MA (US)

( * ) Notice: Subject to any disclaimer, the term of this patent is extended or adjusted under 35 U.S.C. 154(b) by 588 days.

(21) Appl. No.: 14/047,386

(22) Filed: Oct. 7, 2013

(65) Prior Publication Data

US 2014/0034704 A1 Feb. 6, 2014

Related U.S. Application Data

(63) Continuation of application No. 13/419,565, filed on Mar. 14, 2012, now Pat. No. 8,561,873, which is a continuation of application No. 12/579,605, filed on Oct. 15, 2009, now Pat. No. 8,157,151.

(51) Int. Cl.
*A61B 17/072* (2006.01)
*A61B 17/068* (2006.01)

(52) U.S. Cl.
CPC .......... *A61B 17/068* (2013.01); *A61B 17/072* (2013.01); *A61B 17/07207* (2013.01); *A61B 17/07292* (2013.01); *A61B 2017/07214* (2013.01)

(58) Field of Classification Search
CPC ................ A61B 17/068; A61B 17/072; A61B 17/07207; A61B 17/115; A61B 17/1155; A61B 17/07292; A61B 2017/07214

USPC ............. 227/19, 175.1, 176.1, 178.1, 180.1; 606/139, 153, 219

See application file for complete search history.

(56) References Cited

U.S. PATENT DOCUMENTS

| | | |
|---|---|---|
| 3,054,406 A | 9/1962 | Usher |
| 3,079,606 A | 3/1963 | Bobrov et al. |
| 3,124,136 A | 3/1964 | Usher |
| 3,490,675 A | 1/1970 | Green et al. |
| 3,499,591 A | 3/1970 | Green |
| 4,347,847 A | 9/1982 | Usher |
| 4,354,628 A | 10/1982 | Green |
| 4,429,695 A | 2/1984 | Green |
| 4,452,245 A | 6/1984 | Usher |

(Continued)

FOREIGN PATENT DOCUMENTS

| | | |
|---|---|---|
| CA | 2 667 434 | 5/2008 |
| CN | 101310680 A | 11/2008 |
| CN | 101332110 A | 12/2008 |
| DE | 1 99 24 311 | 11/2000 |
| EP | 0 594 148 | 4/1994 |

(Continued)

OTHER PUBLICATIONS

European Office Action corresponding to counterpart Int'l Appln No. EP 12 198 776.2 dated Apr. 7, 2015.

(Continued)

*Primary Examiner* — Scott A. Smith

(57) ABSTRACT

A surgical stapling apparatus including a cartridge assembly defining a first tissue contacting surface, an anvil assembly defining a second tissue contacting surface, and a surgical buttress releasably secured to at least one of the first tissue contacting surface and the second tissue contacting surface is provided. The buttress provides a uniform profile to be used on both the anvil and cartridge of a loading unit.

18 Claims, 10 Drawing Sheets

(56) References Cited

U.S. PATENT DOCUMENTS

| | | |
|---|---|---|
| 4,605,730 A | 8/1986 | Shalaby et al. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,065,929 A | 11/1991 | Schulze et al. |
| 5,205,459 A | 4/1993 | Brinkerhoff et al. |
| 5,263,629 A | 11/1993 | Trumbull et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,405,072 A | 4/1995 | Zlock et al. |
| 5,425,745 A | 6/1995 | Green et al. |
| 5,441,193 A | 8/1995 | Gravener |
| 5,441,507 A | 8/1995 | Wilk et al. |
| 5,443,198 A | 8/1995 | Viola et al. |
| 5,468,253 A | 11/1995 | Bezwada et al. |
| 5,503,638 A | 4/1996 | Cooper et al. |
| 5,542,594 A | 8/1996 | McKean |
| 5,549,628 A | 8/1996 | Cooper et al. |
| 5,575,803 A | 11/1996 | Cooper et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,833,695 A | 11/1998 | Yoon |
| 5,843,096 A | 12/1998 | Igaki et al. |
| 5,871,135 A | 2/1999 | Williamson, IV et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov et al. |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,099,551 A | 8/2000 | Gabbay |
| 6,149,667 A | 11/2000 | Hovland et al. |
| 6,155,265 A | 12/2000 | Hammerslag |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,436,030 B2 | 8/2002 | Rehil |
| 6,454,780 B1 | 9/2002 | Wallace |
| 6,461,368 B2 | 10/2002 | Fogarty et al. |
| 6,503,257 B2 | 1/2003 | Grant et al. |
| 6,514,283 B2 | 2/2003 | DiMatteo et al. |
| 6,517,566 B1 | 2/2003 | Hovland et al. |
| 6,551,356 B2 | 4/2003 | Rousseau |
| 6,592,597 B2 | 7/2003 | Grant et al. |
| 6,638,285 B2 | 10/2003 | Gabbay |
| 6,652,594 B2 | 11/2003 | Francis et al. |
| 6,656,193 B2 | 12/2003 | Grant |
| 6,669,735 B1 | 12/2003 | Pelissier |
| 6,677,258 B2 | 1/2004 | Carroll et al. |
| 6,685,714 B2 | 2/2004 | Rousseau |
| 6,702,828 B2 | 3/2004 | Whayne |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,773,458 B1 | 8/2004 | Brauker et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,959,851 B2 | 11/2005 | Heinrich |
| 7,087,065 B2 | 8/2006 | Ulmsten et al. |
| 7,108,701 B2 | 9/2006 | Evens et al. |
| 7,128,253 B2 | 10/2006 | Mastri |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,210,810 B1 | 5/2007 | Iversen et al. |
| 7,232,449 B2 | 6/2007 | Sharkawy et al. |
| 7,241,300 B2 | 7/2007 | Sharkawy et al. |
| 7,307,031 B2 | 12/2007 | Carroll et al. |
| 7,311,720 B2 | 12/2007 | Mueller et al. |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,594,921 B2 | 9/2009 | Browning |
| 7,604,151 B2 | 10/2009 | Hess et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,717,313 B2 | 5/2010 | Bettuchi et al. |
| 7,722,642 B2 | 5/2010 | Williamson, IV |
| 7,744,627 B2 | 6/2010 | Orban, III et al. |
| 7,776,060 B2 | 8/2010 | Mooradian |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crows et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban |
| 7,967,179 B2 | 6/2011 | Olson |
| 7,988,027 B2 | 8/2011 | Olson |
| 8,011,550 B2 | 9/2011 | Aranyi |
| 8,011,555 B2 | 9/2011 | Tarinelli |
| 8,016,177 B2 | 9/2011 | Bettuchi |
| 8,016,178 B2 | 9/2011 | Olson |
| 8,028,883 B2 | 10/2011 | Stopek |
| 8,062,330 B2 | 11/2011 | Prommersberger |
| 8,083,119 B2 | 12/2011 | Prommersberger |
| 8,123,766 B2 | 2/2012 | Bauman |
| 8,123,767 B2 | 2/2012 | Bauman |

(56) References Cited

U.S. PATENT DOCUMENTS

| | | |
|---|---|---|
| 8,127,975 B2 | 3/2012 | Olson et al. |
| 8,146,791 B2 | 4/2012 | Bettuchi |
| 8,157,149 B2 | 4/2012 | Olson |
| 8,157,151 B2 | 4/2012 | Ingmanson |
| 8,167,895 B2 | 5/2012 | D'Agostino |
| 8,178,746 B2 | 5/2012 | Hildeberg et al. |
| 8,192,460 B2 | 6/2012 | Orban |
| 8,210,414 B2 | 7/2012 | Bettuchi |
| 8,225,799 B2 | 7/2012 | Bettuchi |
| 8,225,981 B2 | 7/2012 | Criscuolo et al. |
| 8,231,043 B2 | 7/2012 | Tarinelli |
| 8,235,273 B2 | 8/2012 | Olson |
| 8,245,901 B2 | 8/2012 | Stopek |
| 8,256,654 B2 | 9/2012 | Bettuchi |
| 8,257,391 B2 | 9/2012 | Orban |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi |
| 8,308,046 B2 | 11/2012 | Prommersberger |
| 8,312,885 B2 | 11/2012 | Bettuchi |
| 8,313,014 B2 | 11/2012 | Bettuchi |
| 8,348,126 B2 | 1/2013 | Olson |
| 8,348,130 B2 | 1/2013 | Shah |
| 8,365,972 B2 | 2/2013 | Aranyi et al. |
| 8,371,491 B2 | 2/2013 | Huitema |
| 8,371,492 B2 | 2/2013 | Aranyi |
| 8,371,493 B2 | 2/2013 | Aranyi |
| 8,393,514 B2 | 3/2013 | Shelton, IV |
| 8,408,440 B2 | 4/2013 | Olson |
| 8,413,869 B2 | 4/2013 | Heinrich |
| 8,413,871 B2 | 4/2013 | Racenet |
| 8,424,742 B2 | 4/2013 | Bettuchi |
| 8,453,652 B2 | 6/2013 | Stopek |
| 8,453,904 B2 | 6/2013 | Eskaros |
| 8,453,909 B2 | 6/2013 | Olson |
| 8,453,910 B2 | 6/2013 | Bettuchi |
| 8,464,925 B2 | 6/2013 | Hull et al. |
| 8,474,677 B2 | 7/2013 | Woodard, Jr. |
| 8,479,968 B2 | 7/2013 | Hodgkinson |
| 8,485,414 B2 | 7/2013 | Criscuolo et al. |
| 8,496,683 B2 | 7/2013 | Prommersberger |
| 8,511,533 B2 | 8/2013 | Viola |
| 8,512,402 B2 | 8/2013 | Marczyk |
| 8,529,600 B2 | 9/2013 | Woodard, Jr. |
| 8,540,131 B2 | 9/2013 | Swayze |
| 8,551,138 B2 | 10/2013 | Orban |
| 8,556,918 B2 | 10/2013 | Bauman |
| 8,561,873 B2 | 10/2013 | Ingmanson |
| 8,584,920 B2 | 11/2013 | Hodgkinson |
| 8,590,762 B2 | 11/2013 | Hess |
| 8,616,430 B2 | 12/2013 | Prommersberger |
| 8,631,989 B2 | 1/2014 | Aranyi |
| 8,646,674 B2 | 2/2014 | Schulte et al. |
| 8,668,129 B2 | 3/2014 | Olson |
| 8,684,250 B2 | 4/2014 | Bettuchi |
| 8,721,703 B2 | 5/2014 | Fowler |
| 8,757,466 B2 | 6/2014 | Olson |
| 8,789,737 B2 | 7/2014 | Hodgkinson |
| 8,820,606 B2 | 9/2014 | Hodgkinson |
| 8,870,050 B2 | 10/2014 | Hodgkinson |
| 8,920,444 B2 | 12/2014 | Hiles et al. |
| 8,939,344 B2 | 1/2015 | Olson et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | (Tarinelli) Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,773 B2 | 5/2016 | Casasanta, Jr. et al. |
| 9,345,479 B2 | 5/2016 | (Tarinelli) Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,364,229 B2 | 6/2016 | D'Agostino et al. |
| 9,364,234 B2 | 6/2016 | (Prommersberger) Stopek et al. |
| 2002/0028243 A1 | 3/2002 | Masters |
| 2002/0091397 A1 | 7/2002 | Chen |
| 2002/0151911 A1 | 10/2002 | Gabbay |
| 2002/0165563 A1 | 11/2002 | Grant et al. |
| 2003/0065345 A1 | 4/2003 | Weadock |
| 2003/0083676 A1 | 5/2003 | Wallace |
| 2003/0120284 A1 | 6/2003 | Palacios |
| 2003/0181927 A1 | 9/2003 | Wallace |
| 2003/0183671 A1 | 10/2003 | Mooradian et al. |
| 2003/0196668 A1 | 10/2003 | Harrison et al. |
| 2003/0208231 A1 | 11/2003 | Williamson, IV et al. |
| 2004/0107006 A1 | 6/2004 | Francis et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0143756 A1 | 6/2005 | Jankowski |
| 2005/0149073 A1 | 7/2005 | Arani et al. |
| 2006/0004407 A1 | 1/2006 | Hiles et al. |
| 2006/0085030 A1 | 4/2006 | Bettuchi et al. |
| 2006/0135992 A1 | 6/2006 | Bettuchi |
| 2006/0173470 A1 | 8/2006 | Oray et al. |
| 2006/0178683 A1 | 8/2006 | Shimoji et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0243227 A1 | 10/2007 | Gertner |
| 2007/0246505 A1 | 10/2007 | Pace-Floridia et al. |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |

(56) References Cited

U.S. PATENT DOCUMENTS

| | | |
|---|---|---|
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0200949 A1 | 8/2008 | Hiles |
| 2008/0216855 A1 | 9/2008 | Nasca |
| 2008/0220047 A1 | 9/2008 | Sawhney et al. |
| 2008/0230583 A1 | 9/2008 | Heinrich |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0092651 A1* | 4/2009 | Shah ..................... A61L 27/34 424/422 |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0277944 A9 | 11/2009 | Dalessandro et al. |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0065606 A1 | 3/2010 | Stopek |
| 2010/0065607 A1 | 3/2010 | Orban, III et al. |
| 2010/0072254 A1 | 3/2010 | Aranyi et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2010/0331880 A1 | 12/2010 | Stopek |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0087279 A1 | 4/2011 | Shah et al. |
| 2011/0215132 A1 | 9/2011 | Aranyi |
| 2012/0074199 A1 | 3/2012 | Olson |
| 2012/0080336 A1 | 4/2012 | Shelton |
| 2012/0083723 A1 | 4/2012 | Vitaris et al. |
| 2012/0187179 A1 | 7/2012 | Gleiman |
| 2012/0197272 A1 | 8/2012 | Oray et al. |
| 2012/0241499 A1 | 9/2012 | Baxter |
| 2012/0273547 A1 | 11/2012 | Hodgkinson et al. |
| 2013/0037596 A1 | 2/2013 | Bear et al. |
| 2013/0105548 A1 | 5/2013 | Hodgkinson |
| 2013/0105553 A1 | 5/2013 | Racenet |
| 2013/0112732 A1 | 5/2013 | Aranyi |
| 2013/0112733 A1 | 5/2013 | Aranyi |
| 2013/0146641 A1 | 6/2013 | Shelton |
| 2013/0153633 A1 | 6/2013 | Casasanta |
| 2013/0153634 A1 | 6/2013 | Carter |
| 2013/0153635 A1 | 6/2013 | Hodgkinson |
| 2013/0153636 A1 | 6/2013 | Shelton |
| 2013/0153638 A1 | 6/2013 | Carter |
| 2013/0153639 A1 | 6/2013 | Hodgkinson |
| 2013/0153640 A1 | 6/2013 | Hodgkinson |
| 2013/0153641 A1 | 6/2013 | Shelton, IV et al. |
| 2013/0161374 A1 | 6/2013 | Swayze |
| 2013/0181031 A1 | 7/2013 | Olson |
| 2013/0193186 A1 | 8/2013 | Racenet |
| 2013/0193190 A1 | 8/2013 | Carter |
| 2013/0193191 A1 | 8/2013 | Stevenson |
| 2013/0193192 A1 | 8/2013 | Casasanta |
| 2013/0209659 A1 | 8/2013 | Racenet |
| 2013/0221062 A1 | 8/2013 | Hodgkinson |
| 2013/0240600 A1 | 9/2013 | Bettuchi |
| 2013/0240601 A1 | 9/2013 | Bettuchi |
| 2013/0240602 A1 | 9/2013 | Stopek |
| 2013/0256380 A1 | 10/2013 | Schmid et al. |
| 2013/0277411 A1 | 10/2013 | Hodgkinson |
| 2013/0306707 A1 | 11/2013 | Viola |
| 2013/0310873 A1 | 11/2013 | Prommersberger |
| 2013/0327807 A1 | 12/2013 | Olson |
| 2014/0012317 A1 | 1/2014 | Orban |
| 2014/0021242 A1 | 1/2014 | Hodgkinson |
| 2014/0027490 A1 | 1/2014 | Marczyk |
| 2014/0048580 A1 | 2/2014 | Merchant |
| 2014/0061280 A1 | 3/2014 | Ingmanson |
| 2014/0061281 A1 | 3/2014 | Hodgkinson |
| 2014/0084042 A1 | 3/2014 | Stopek |
| 2014/0097224 A1 | 4/2014 | Prior |
| 2014/0117066 A1 | 5/2014 | Aranyi |
| 2014/0130330 A1 | 5/2014 | Olson |
| 2014/0131418 A1 | 5/2014 | Kostrzewski |
| 2014/0131419 A1 | 5/2014 | Bettuchi |
| 2014/0138423 A1 | 5/2014 | Whitfield |
| 2014/0151431 A1 | 6/2014 | Hodgkinson |
| 2014/0155916 A1 | 6/2014 | Hodgkinson |
| 2014/0158742 A1 | 6/2014 | Stopek |
| 2014/0166721 A1 | 6/2014 | Stevenson |
| 2014/0197224 A1 | 7/2014 | Penna |
| 2014/0203061 A1 | 7/2014 | Hodgkinson |
| 2014/0217147 A1 | 8/2014 | Milliman |
| 2014/0217148 A1 | 8/2014 | Penna |
| 2014/0239046 A1 | 8/2014 | Milliman |
| 2014/0239047 A1 | 8/2014 | Hodgkinson |
| 2014/0252062 A1 | 9/2014 | Mozdzierz |
| 2015/0001276 A1 | 1/2015 | Hodgkinson et al. |
| 2015/0041347 A1 | 2/2015 | Hodgkinson |
| 2015/0097018 A1 | 4/2015 | Hodgkinson |
| 2015/0115015 A1 | 4/2015 | Prescott et al. |
| 2015/0122872 A1 | 5/2015 | Olson et al. |
| 2015/0164503 A1 | 6/2015 | Stevenson et al. |
| 2015/0164506 A1 | 6/2015 | Carter et al. |
| 2015/0164507 A1 | 6/2015 | Carter et al. |
| 2015/0196297 A1 | 7/2015 | (Prommersberger) Stopek et al. |
| 2015/0209033 A1 | 7/2015 | Hodgkinson |
| 2015/0209045 A1 | 7/2015 | Hodgkinson et al. |
| 2015/0209048 A1 | 7/2015 | Carter et al. |
| 2015/0305743 A1 | 10/2015 | Casasanta et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0058451 A1 | 3/2016 | (Tarinelli) Racenet et al. |
| 2016/0100834 A1 | 4/2016 | Viola et al. |
| 2016/0106430 A1 | 4/2016 | Carter et al. |
| 2016/0113647 A1 | 4/2016 | Hodgkinson |
| 2016/0157857 A1 | 6/2016 | Hodgkinson et al. |
| 2016/0174988 A1 | 6/2016 | D'Agostino et al. |

FOREIGN PATENT DOCUMENTS

| | | |
|---|---|---|
| EP | 0 327 022 | 4/1995 |
| EP | 0 667 119 | 8/1995 |
| EP | 1 064 883 | 1/2001 |
| EP | 1 256 317 | 11/2002 |
| EP | 1 256 318 | 11/2002 |
| EP | 1 520 525 | 4/2005 |

(56) References Cited

FOREIGN PATENT DOCUMENTS

| | | |
|---|---|---|
| EP | 1 621 141 | 2/2006 |
| EP | 1 702 570 | 9/2006 |
| EP | 1 759 640 | 3/2007 |
| EP | 1 815 804 | 8/2007 |
| EP | 1 825 820 | 8/2007 |
| EP | 1 929 958 | 6/2008 |
| EP | 1 994 890 | 11/2008 |
| EP | 2 005 894 | 12/2008 |
| EP | 2 005 895 | 12/2008 |
| EP | 2 008 595 | 12/2008 |
| EP | 2 039 308 A2 | 3/2009 |
| EP | 2 090 231 | 8/2009 |
| EP | 2 090 244 | 8/2009 |
| EP | 2 090 252 | 8/2009 |
| EP | 2 163 211 A2 | 3/2010 |
| EP | 2 189 121 A1 | 5/2010 |
| EP | 2 198 787 | 6/2010 |
| EP | 2 236 098 | 10/2010 |
| EP | 2 236 099 | 10/2010 |
| EP | 2 258 282 A2 | 12/2010 |
| EP | 2 292 276 A2 | 3/2011 |
| EP | 2 311 386 | 4/2011 |
| EP | 2 311 386 A2 | 4/2011 |
| EP | 2 436 348 | 4/2012 |
| EP | 2 462 880 | 6/2012 |
| EP | 2 497 431 A1 | 9/2012 |
| EP | 2 517 637 | 10/2012 |
| EP | 2 586 380 | 5/2013 |
| EP | 2 604 195 | 6/2013 |
| EP | 2 604 197 | 6/2013 |
| EP | 2 620 105 A1 | 7/2013 |
| EP | 2 620 106 | 7/2013 |
| EP | 2 630 922 | 8/2013 |
| EP | 2 644 125 | 10/2013 |
| EP | 2 705 800 A1 | 3/2014 |
| EP | 2 762 091 A2 | 8/2014 |
| JP | 2000-166933 | 6/2000 |
| JP | 2002-202213 | 7/2002 |
| JP | 2006043451 A | 2/2006 |
| JP | 2007-124166 | 5/2007 |
| JP | 2008289883 A | 12/2008 |
| JP | 2008307393 A | 12/2008 |
| JP | 2009000531 A | 1/2009 |
| JP | 2010148879 A | 7/2010 |
| JP | 2010240429 A | 10/2010 |
| WO | WO 90/05489 | 5/1990 |
| WO | WO 95/16221 | 6/1995 |
| WO | WO 96/22055 | 7/1996 |
| WO | WO 97/01989 | 1/1997 |
| WO | WO 97/13463 | 4/1997 |
| WO | WO 98/17180 | 4/1998 |
| WO | 98/38923 A1 | 9/1998 |
| WO | WO 99/45849 | 9/1999 |
| WO | WO 03/082126 | 10/2003 |
| WO | WO 03/088845 | 10/2003 |
| WO | WO 03/094743 | 11/2003 |
| WO | WO 03/105698 | 12/2003 |
| WO | WO 2005/079675 | 9/2005 |
| WO | WO 2006/023578 | 3/2006 |
| WO | WO 2006/044490 | 4/2006 |
| WO | WO 2006/083748 | 8/2006 |
| WO | WO 2007/121579 | 11/2007 |
| WO | WO 2008/057281 | 5/2008 |
| WO | WO 2008/109125 | 9/2008 |
| WO | WO 2010/075298 | 7/2010 |
| WO | WO 2011/143183 | 11/2011 |
| WO | WO 2012/044848 | 4/2012 |

OTHER PUBLICATIONS

European Office Action corresponding to counterpart Int'l Appln No. EP 13 156 297.7 dated Apr. 10, 2015.
Australian Examination Report No. 1 corresponding to counterpart Int'l Appln No. AU 2011250822 dated May 18, 2015.
European Office Action corresponding to counterpart Int'l Appln No. EP 12 186 175.1 dated Jun. 1, 2015.
Chinese Office Action corresponding to counterpart Int'l Appln No. CN 201010517292.8 dated Jun. 2, 2015.
Extended European Search Report corresponding to counterpart Int'l Appln No. EP 14 17 4814.5 dated Jun. 9, 2015.
Australian Examination Report No. 1 corresponding to counterpart Int'l Appln No. AU 2014200584 dated Jun. 15, 2015.
European Office Action corresponding to counterpart Int'l Appln No. EP 13 180 881.8 dated Jun. 19, 2015.
European Office Action corresponding to counterpart Int'l Appln No. EP 14 157 195.0 dated Jul. 2, 2015.
Extended European Search Report corresponding to counterpart Int'l Appln No. EP 12 19 6902.6 dated Aug. 6, 2015.
Extended European Search Report corresponding to counterpart Int'l Appln No. EP 14 15 2060.1 dated Aug. 14, 2015.
Chinese Office Action corresponding to counterpart Int'l Appln No. CN 201210129787.2 dated Aug. 24, 2015.
Extended European Search Report corresponding to EP 13 17 7437.4, completed Sep. 11, 2013 and mailed Sep. 19, 2013; (6 pp).
Extended European Search Report corresponding to EP 13 17 7441.6, completed Sep. 11, 2013 and mailed Sep. 19, 2013; (6 pp).
Extended European Search Report corresponding to EP 07 86 1534.1, completed Sep. 20, 2013 and mailed Sep. 30, 2013; (5 pp).
Extended European Search Report corresponding to EP 13 18 3876.5, completed Oct. 14, 2013 and mailed Oct. 24, 2013; (5 pp).
Extended European Search Report corresponding to EP 13 17 1856.1, completed Oct. 29, 2013 and mailed Nov. 7, 2013; (8 pp).
Extended European Search Report corresponding to EP 13 18 0373.6, completed Oct. 31, 2013 and mailed Nov. 13, 2013; (7 pp).
Extended European Search Report corresponding to EP 13 18 0881.8, completed Nov. 5, 2013 and mailed Nov. 14, 2013; (6 pp).
Extended European Search Report corresponding to EP 13 17 6895.4, completed Nov. 29, 2013 and mailed Dec. 12, 2013; (5 pp).
Extended European Search Report corresponding to EP 13 18 7911.6, completed Jan. 22, 2014 and mailed Jan. 31, 2014; (8 pp).
Extended European Search Report corresponding to EP 14 16 9739.1, completed Aug. 19, 2014 and Aug. 29, 2014; (7 pp).
Extended European Search Report corresponding to EP 14 15 7997.9, completed Sep. 9, 2014 and mailed Sep. 17, 2014; (8 pp).
Extended European Search Report corresponding to EP 14 16 8904.2, completed Sep. 10, 2014 and mailed Sep. 18, 2014; (8 pp).
Extended European Search Report corresponding to EP 13 19 4995.0, completed Jun. 5, 2014 and mailed Oct. 13, 2014; (10 pp).
Extended European Search Report corresponding to EP 13 15 4571.7, completed Oct. 10, 2014 and mailed Oct. 20, 2014; (8 pp).
Extended European Search Report corresponding to EP 14 18 1125.7, completed Oct. 16, 2014 and mailed Oct. 24, 2014; (7 pp).
Extended European Search Report corresponding to EP 14 18 1127.3, completed Oct. 16, 2014 and mailed Nov. 10, 2014; (8 pp).
Extended European Search Report corresponding to EP 14 19 0419.3, completed Mar. 24, 2015 and mailed Mar. 30, 2015; (6 pp).
Extended European Search Report corresponding to EP 14 17 4814.5 completed Jun. 1, 2015 and mailed Jun. 9, 2015; (8 pp).
Chinese Office Action corresponding to CN 201010517292.8 dated Jun. 2, 2015; (13 pp).
Australian Examination Report corresponding to AU 2010224378 dated Jun. 15, 2015; (2 pp).
Extended European Search Report corresponding to EP 08 72 6500.5, completed Feb. 20, 2014 and mailed Mar. 3, 2014; (7 pp).
Extended European Search Report corresponding to EP 13 19 5919.9, completed Feb. 10, 2014 and mailed Mar. 3, 2014; (7 pp).
Extended European Search Report corresponding to EP 13 19 2123.1, completed Jan. 30, 2014 and mailed Feb. 10, 2014; (8 pp).
Extended European Search Report corresponding to EP 13 19 6816.6, completed Mar. 28, 2014 and mailed Apr. 9, 2014; (9 pp).
Extended European Search Report corresponding to EP 13 19 4995.0, completed Jun. 5, 2014 and mailed Jun. 16, 2014; (5 pp).
Extended European Search Report corresponding to EP 13 19 5019.8, completed Mar. 14, 2014 and mailed Mar. 24, 2014; (7 pp).
Extended European Search Report corresponding to EP 13 19 2111.6, completed Feb. 13, 2014 and mailed Feb. 27, 2014; (10 pp)

(56) References Cited

OTHER PUBLICATIONS

Extended European Search Report corresponding to EP 13 19 7958.5, completed Apr. 4, 2014 and mailed Apr. 15, 2014; (8 pp).
Extended European Search Report corresponding to EP 14 15 6342.9, completed Jul. 22, 2014 and mailed Jul. 29, 2014; (8 pp).
Extended European Search Report corresponding to EP 14 15 7195.0, completed Jun. 5, 2014 and mailed Jun. 18, 2014; (9 pp).
Japanese Office Action corresponding to counterpart application JP 2014-216989 mailed Sep. 11, 2015.
European Search Report corresponding to EP 05 02 2585.3, completed Jan. 25, 2006 and mailed Feb. 3, 2006; 4 pages.
European Search Report corresponding to EP 06 00 4598, completed Jun. 22, 2006; 2 pages.
European Search Report corresponding to EP 06 01 6962.0, completed Jan. 3, 2007 and mailed Jan. 11, 2007; 10 pages.
International Search Report corresponding to International Application No. PCT/US2005/036740, completed Feb. 20, 2007 and mailed Mar. 23, 2007; 8 pages.
International Search Report corresponding to International Application No. PCT/US2007/022713, completed Apr. 21, 2008 and mailed May 15, 2008; 1 pages.
International Search Report corresponding to International Application No. PCT/US2008/002981, completed Jun. 9, 2008 and mailed Jun. 26, 2008; 2 pages.
European Search Report corresponding to EP 08 25 1779, completed Jul. 14, 2008 and mailed Jul. 23, 2008; 5 pages.
European Search Report corresponding to EP 08 25 1989.3, completed Mar. 11, 2010 and mailed Mar. 24, 2010; 6 pages.
European Search Report corresponding to EP 10 25 0639.1, completed Jun. 17, 2010 and mailed Jun. 28, 2010; 7 pages.
European Search Report corresponding to EP 10 25 0715.9, completed Jun. 30, 2010 and mailed Jul. 20, 2010; 3 pages.
European Search Report corresponding to EP 05 80 4382.9, completed Oct. 5, 2010 and mailed Oct. 12, 2010; 3 pages.
European Search Report corresponding to EP 10 25 1437.9, completed Nov. 22, 2010 and mailed Dec. 16, 2010; 3 pages.
European Search Report corresponding to EP 09 25 2897.5, completed Feb. 7, 2011 and mailed Feb. 15, 2011; 3 pages.
European Search Report corresponding to EP 10 25 0642.5, completed Mar. 25, 2011 and mailed Apr. 4, 2011; 4 pages.
European Search Report corresponding to EP 11 18 8309.6, completed Dec. 15, 2011 and mailed Jan. 12, 2012; 3 pages.
European Search Report corresponding to EP 12 15 2229.6, completed Feb. 23, 2012 and mailed Mar. 1, 2012; 4 pages.
European Search Report corresponding to EP 12 15 0511.9, completed Apr. 16, 2012 and mailed Apr. 24, 2012; 7 pages.
European Search Report corresponding to EP 12 15 2541.4, completed Apr. 23, 2012 and mailed May 3, 2012; 10 pages.
European Search Report corresponding to EP 12 16 5609.4, completed Jul. 5, 2012 and mailed Jul. 13, 2012; 8 pages.
European Search Report corresponding to EP 12 15 8861.0, completed Jul. 17, 2012 and mailed Jul. 24, 2012; 9 pages.
European Search Report corresponding to EP 12 16 5878.5, completed Jul. 24, 2012 and mailed Aug. 6, 2012; 8 pages.
Extended European Search Report corresponding to EP 12 19 1035.0, completed Jan. 11, 2013 and mailed Jan. 18, 2013; 7 pages.
Extended European Search Report corresponding to EP 12 18 6175.1, completed Jan. 15, 2013 and mailed Jan. 23, 2013; 7 pages.
Extended European Search Report corresponding to EP 12 19 1114.3, completed Jan. 23, 2013 and mailed Jan. 31, 2013; 10 pages.
Extended European Search Report corresponding to EP 12 19 2224.9, completed Mar. 14, 2013 and mailed Mar. 26, 2013; 8 pages.
Extended European Search Report corresponding to EP 12 19 6904.2, completed Mar. 28, 2013 and mailed Jul. 26, 2013; 8 pages.
Extended European Search Report corresponding to EP 12 19 6911.7, completed Apr. 18, 2013 and mailed Apr. 24, 2013; 8 pages.
Extended European Search Report corresponding to EP 07 00 5842.5, completed May 13, 2013 and mailed May 29, 2013; 7 pages.
Extended European Search Report corresponding to EP 12 19 8776.2, completed May 16, 2013 and mailed May 27, 2013; 8 pages.
Extended European Search Report corresponding to EP 12 19 8749.9, completed May 21, 2013 and mailed May 31, 2013; 8 pages.
Extended European Search Report corresponding to EP 13 15 6297.7, completed Jun. 4, 2013 and mailed Jun. 13, 20131; 7 pages.
Extended European Search Report corresponding to EP 13 17 3985.6, completed Aug. 19, 2013 and mailed Aug. 28, 2013; 6 pages.
Extended European Search Report corresponding to EP 13 17 3986.4, completed Aug. 20, 2013 and mailed Aug. 29, 2013; 7 pages.
Extended European Search Report corresponding to EP 13 18 2911.1, completed Dec. 2, 2013 and mailed Dec. 16, 2013; 8 pages.
Extended European Search Report corresponding to EP 10 25 1795.0, completed Dec. 11, 2013 and mailed Dec. 20, 2013; 6 pages.
Canadian Office Action corresponding to counterpart Int'l Appln. No. CA 2,717,683 dated Jun. 17, 2016.
Chinese Office Action corresponding to counterpart Int'l Appln. No. CN 201410778512.0, dated May 13, 2016.
Chinese Notification of Reexamination corresponding to counterpart Int'l Appln. No. CN 201010517292.8 dated Jun. 2, 2015.
Extended European Search Report corresponding to counterpart Int'l Appln. No. EP 14 15 2060.1 dated Aug. 14, 2015.
Japanese Office Action corresponding to counterpart Int'l Appln. No. JP 2014-216989 mailed Sep. 11, 2015.
Canadian First Office Action corresponding to counterpart Int'l Appln. No. CA 2,686,105 dated Sep. 17, 2015.
Japanese Office Action corresponding to counterpart Int'l Appln. No. JP 2012-040188 mailed Oct. 21, 2015.
European Communication corresponding to counterpart Int'l Appln. No. EP 13 17 6895.4 dated Nov. 5, 2015.
Chinese First Office Action corresponding to counterpart Int'l Appln. No. CN 201210544552 dated Nov. 23, 2015.
Chinese First Office Action corresponding to counterpart Int'l Appln. No. CN 201210545228 dated Nov. 30, 2015.
Extended European Search Report corresponding to counterpart Int'l Appln. No. EP 15 18 0491.1 dated Dec. 9, 2015.
Extended European Search Report corresponding to counterpart Int'l Appln. No. EP 15 18 3819.0 dated Dec. 11, 2015.
Canadian Office Action corresponding to counterpart Int'l Appln. No. CA 2,697,819 dated Jan. 6, 2016.
Canadian Office Action corresponding to counterpart Int'l Appln. No. CA 2,696,419 dated Jan. 14, 2016.
European Office Action corresponding to counterpart Int'l Appln. No. EP 12 19 8776.2 dated Jan. 19, 2016.
Extended European Search Report corresponding to counterpart Int'l Appln. No. EP 15 17 4146.9 dated Jan. 20, 2016.
Chinese First Office Action corresponding to counterpart Int'l Appln. No. CN 201310353628.5 dated Jan. 25, 2016.
Extended European Search Report corresponding to counterpart Int'l Appln. No. EP 12 19 6912.5 dated Feb. 1, 2016.
Japanese Office Action corresponding to counterpart Int'l Appln. No. JP 2012-098903 mailed Feb. 22, 2016.
Extended European Search Report corresponding to counterpart Int'l Appln. No. EP 12 19 8753.1 dated Feb. 24, 2016.
Chinese First Office Action corresponding to counterpart Int'l Appln. No. CN 201410449019.4 dated Mar. 30, 2016.
Extended European Search Report corresponding to counterpart Int'l Appln. No. EP 16 15 0232.3 dated Apr. 12, 2016.
European Office Action corresponding to counterpart Int'l Appln. No. EP 11 18 3256.4 dated Apr. 20, 2016.
Australian Examination Report No. 1 corresponding to counterpart Int'l Appln. No. AU 2012244169 dated May 10, 2016.
European Office Action corresponding to counterpart Int'l Appln. No. EP 10 25 0715.9 dated May 12, 2016.
Chinese First Office Action corresponding to counterpart Int'l Appln. No. CN 201410778512.0 dated May 13, 2016.
Australian Examination Report No. 1 corresponding to counterpart Int'l Appln. No. AU 2012227358 dated May 16, 2016.
Japanese Office Action corresponding to counterpart Int'l Appln. No. JP 2012-040188 mailed May 17, 2016.

(56) References Cited

OTHER PUBLICATIONS

Australian Examination Report No. 1 corresponding to counterpart Int'l Appln. No. AU 2012244380 dated May 20, 2016.
Australian Examination Report No. 1 corresponding to counterpart Int'l Appln. No. AU 2014227480 dated May 21, 2016.
Australian Examination Report No. 1 corresponding to counterpart Int'l Appln. No. AU 2012254977 dated May 30, 2016.
Extended European Search Report corresponding to counterpart Int'l Appln. No. EP 16 15 3647.9 dated Jun. 3, 2016.
European Office Action corresponding to counterpart Int'l Appln. No. EP 15 15 2392.5 dated Aug. 8, 2016.

* cited by examiner

STAPLE LINE REINFORCEMENT FOR ANVIL AND CARTRIDGE

CROSS-REFERENCE TO RELATED APPLICATIONS

This application is a continuation of U.S. patent application Ser. No. 13/419,565, filed Mar. 14, 2012, now U.S. Pat. No. 8,561,873 which is a continuation of U.S. patent application Ser. No. 12/579,605, filed Oct. 15, 2009, now U.S. Pat. No. 8,157,151 and the disclosures of each of the above-identified applications are hereby incorporated by reference in their entirety.

BACKGROUND

1. Technical Field

The present disclosure relates to a surgical stapling apparatus and, more particularly, to a surgical stapling apparatus including a detachable surgical buttress for an anvil and a staple cartridge.

2. Background of Related Art

Surgical stapling instruments that are used to sequentially or simultaneously apply one or more rows of fasteners to join segments of body tissues are well known in the art. The fasteners are typically in the form of surgical staples but two part polymeric fasteners can also be utilized. Such devices generally include a pair of jaws to clamp therebetween the body tissues to be joined. Typically, one of the jaw members includes a staple cartridge which accommodates a plurality of staples arranged in at least two lateral rows while the other jaw member has an anvil that defines a surface for forming the staple legs as the staples are driven from the staple cartridge.

When the stapling instrument is actuated, longitudinally translating cams contact staple drive members in one of the jaws which in turn acts upon staple pushers to sequentially or simultaneously eject the staples from the staple cartridge. A blade can travel between the staple rows to longitudinally cut and/or open the stapled tissue between the rows of staples. Such instruments are disclosed, for example, in U.S. Pat. No. 3,079,606 and U.S. Pat. No. 3,490,675.

When stapling relatively thin or fragile tissues, it is important to effectively seal the staple line against air or fluid leakage. Additionally, it is often necessary to reinforce the staple line against the tissue to prevent tears in the tissue or pulling of the staples through the tissue. One method of preventing tears or pull through involves the placement of a biocompatible fabric reinforcing material, or a "buttress," between the staple and the underlying tissue. In this method, a layer of buttress material is placed against the tissue and the tissue is stapled in conventional manner. In more recent methods, the layer of buttress is positioned on the stapling instrument itself prior to stapling the tissue. Some surgical staplers utilize fasteners or clips to temporarily connect buttress material to each of the jaws of the staplers, i.e., one disposed on the staple cartridge assembly and the other on the anvil assembly.

It is a desire of the present application to provide a staple line reinforcement profile which simultaneously incorporates features which satisfy the requirements of one or more different assemblies. It would also be desirable to provide a single profile buttress that can be used on a surgical staple cartridge assembly and/or a surgical anvil cartridge assembly. Accordingly, it is an object of this disclosure to meet the aforementioned desires.

SUMMARY

The present disclosure relates to a surgical stapling apparatus including a surgical buttress.

According to an aspect of the present disclosure, a surgical stapling apparatus is provided and includes a cartridge assembly defining a first tissue contacting surface, the cartridge assembly housing a plurality of surgical fasteners therein, the cartridge assembly defining at least one distal attachment point and at least one proximal attachment point; an anvil assembly defining a second tissue contacting surface, the anvil assembly movably secured in relation to cartridge assembly, the anvil assembly defining at least one distal attachment point and at least one proximal attachment point, wherein the at least one proximal attachment point of the anvil assembly is offset an axial distance from the at least one proximal attachment point of the cartridge assembly; and a surgical buttress releasably secured to each of the first tissue contacting surface and the second tissue contacting surface, the surgical buttress including a body portion configured to substantially overlie at least one of the first and second tissue contacting surfaces of either the first length and second length cartridge assembly and anvil assembly.

Each surgical buttress defines a distal attachment feature for registration with the distal attachment point of the cartridge assembly and the anvil assembly; and a first proximal attachment feature and a second proximal attachment feature offset an axial distance from the first proximal attachment feature. The first proximal attachment feature registers with the proximal attachment point of the cartridge assembly; and the second proximal attachment feature registers with the proximal attachment point of the anvil assembly.

The surgical buttress may be disposed against the tissue contact surface of the cartridge assembly and the surgical buttress may be disposed against the tissue contact surface of the anvil assembly have substantially the same length.

Each surgical buttress may have the same configuration. Each surgical buttress may be fabricated from a biocompatible and bioabsorbable material.

The surgical stapling apparatus may further include sutures retaining surgical buttresses against the tissue contacting surface of the cartridge assembly and the anvil assembly.

The surgical stapling apparatus may further include a suture retaining a distal end portion of the surgical buttress against a respective one of the cartridge assembly and the anvil assembly, wherein the suture maintains the distal attachment feature of the surgical buttress in registration with the distal attachment point of the respective one of the cartridge assembly and the anvil assembly.

The surgical stapling apparatus may further include a suture retaining a proximal end portion of the surgical buttress against a respective one of the cartridge assembly and the anvil assembly, wherein a suture maintains the first proximal attachment feature of the surgical buttress in registration with the proximal attachment point of the cartridge assembly and the anvil assembly, and wherein a suture maintains the second proximal attachment feature of the surgical buttress in registration with the proximal attachment point of the anvil assembly.

According to another aspect of the present disclosure, a surgical stapling apparatus is provided and includes a cartridge assembly defining a first tissue contacting surface, the cartridge assembly housing a plurality of surgical fasteners therein, the cartridge assembly being either a first length or a second length longer than the first length; an anvil assembly defining a second tissue contacting surface, the anvil assembly movably secured in relation to cartridge assembly, the anvil assembly being either the first length or the second length each corresponding to the length of the cartridge assembly; and a surgical buttress releasably secured to at least one of the first tissue contacting surface and the second tissue contacting surface, the surgical buttress including a head portion, a neck portion, and a body portion. The head portion is connected to a distal end of the body portion by the neck portion. The surgical buttress is configured to substantially overlie at least one of the first and second tissue contacting surfaces of either the first length and second length cartridge assembly and anvil assembly.

The body portion of the surgical buttress may define a recess formed in a proximal edge thereof, the recess longitudinally bisecting the proximal edge. The recess may be a notch having a v-shape profile.

The body portion of the surgical buttress may define at least one pair of opposing proximal recesses, and each of the at least one pair of opposing proximal recesses may be formed on an opposing lateral side of the body portion near a proximal edge of the surgical buttress. The at least one pair of opposing proximal recesses may be a notch having a v-shape profile.

The body portion of the surgical buttress may further define a pair of opposing distal recesses, and each of the pair of opposing distal recesses may be formed on an opposing lateral side of the body portion near a distal edge of the body portion.

The pair of opposing distal recesses may be longitudinally tapered. A distal edge of the body portion of the surgical buttress may be arcuated. A distal edge of the body portion of the surgical buttress may have a transverse width dimension less than that of the rest of the body portion. The head portion may have a substantially rectangular shape.

Each surgical buttress may be fabricated from a biocompatible and bioabsorbable material.

According to a further aspect of the present disclosure, a surgical buttress for use in a surgical stapling apparatus is provided. The surgical buttress includes a body portion; a neck portion; and a head portion connected to a distal end of the body portion by the neck portion, wherein the body portion defines at least one pair of opposing proximal recesses, each of the at least one pair of opposing proximal recesses is formed on an opposing lateral side of the body portion near a proximal edge of the body portion.

Each of the at least one pair of opposing proximal recesses may be a notch having a v-shape profile. The body portion may further define a pair of opposing distal recesses, each of the pair of opposing distal recesses may be formed on an opposing lateral side of the body portion near a distal edge of the body portion.

The body portion of the surgical buttress may further define a proximal edge recess formed in a proximal edge thereof, the proximal edge recess longitudinally bisecting the proximal edge. A distal edge of the body portion of the surgical buttress may be arcuated. A distal edge of the body portion of the surgical buttress may have a transverse width dimension less than that of the rest of the body portion. The head portion may have a substantially rectangular shape.

The surgical buttress may be fabricated from a biocompatible and bioabsorbable material.

According to still another aspect of the present disclosure, a surgical buttress is provided for use with a surgical stapling apparatus having a cartridge assembly of any number of lengths and an anvil assembly of any number of lengths corresponding to the lengths of the cartridge assembly, wherein each of the cartridge assembly and anvil assembly defines respective juxtaposed tissue contacting surfaces, and wherein the cartridge assembly includes a plurality of staples stored in staple slots thereof for formation against staple formation pockets of the anvil assembly. The surgical buttress includes a body portion configured and dimensioned to overlie all of the staple slots of the cartridge assembly for any length cartridge assembly, and/or overlie all of the staple formation pockets of the anvil assembly for any length anvil assembly. The surgical buttress further includes a neck portion extending from the body portion; and a head portion connected to the neck portion and opposite a distal end of the body portion, wherein the body portion defines at least one pair of opposing proximal recesses, each of the at least one pair of opposing proximal recesses is formed on an opposing lateral side of the body portion near a proximal edge of the body portion.

BRIEF DESCRIPTION OF THE DRAWINGS

The present disclosure will be further described with reference to the accompanying drawings, wherein like reference numerals refer to like parts in the several views, and wherein.

DETAILED DESCRIPTION OF EMBODIMENTS

Figure 1:
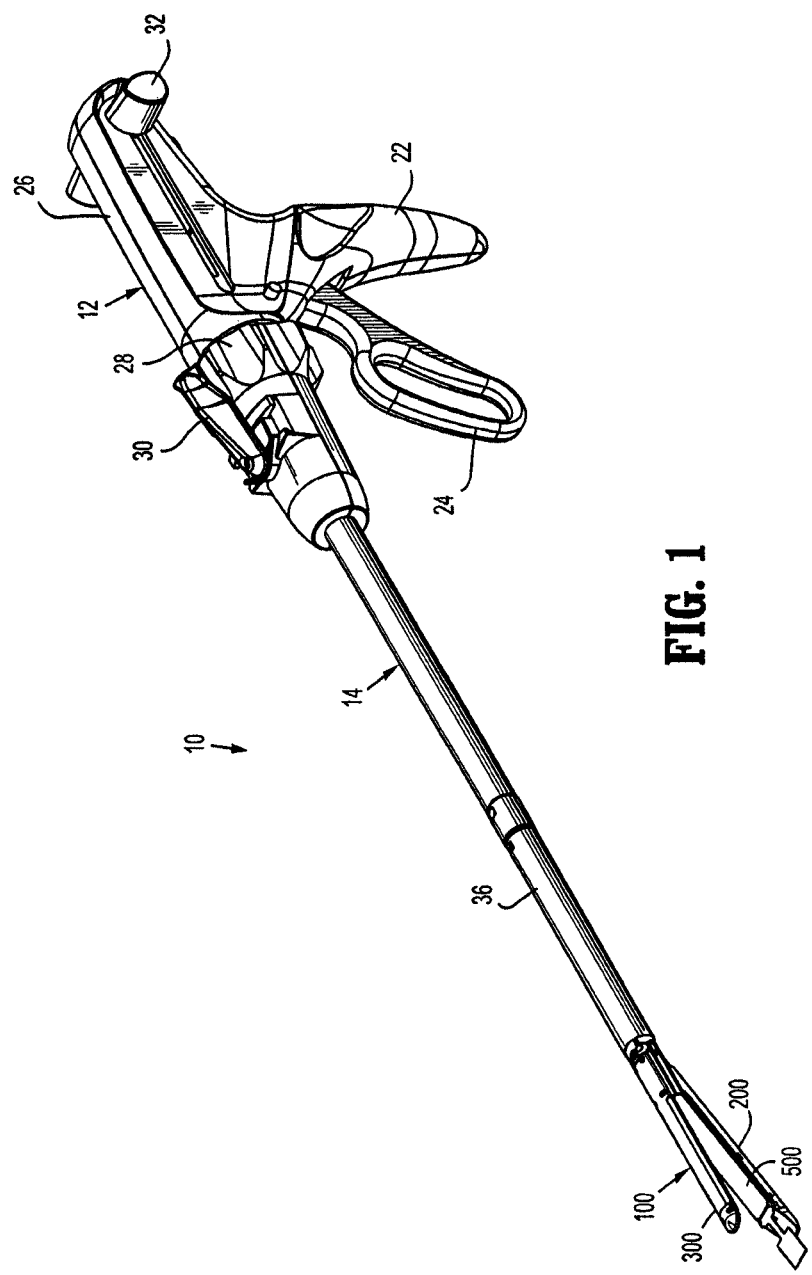
FIG. 1 is a perspective view of a surgical stapling apparatus according to an embodiment of the present disclosure.

Embodiments of the presently disclosed staple line reinforcement for anvil and cartridge of a loading unit of a surgical stapling apparatus will now be described in detail with reference to the drawings, in which like reference numerals designate identical or corresponding elements in each of the several views. In the drawings and in the description that follows, the term "proximal," as is traditional, will refer to the end of the stapling apparatus which is closest to the operator, while the term "distal" will refer to the end of the apparatus which is farthest from the operator.

Referring now to FIG. 1, there is disclosed a linear surgical stapling apparatus, generally referred to as 10. In the interest of brevity, this disclosure will focus primarily on a buttress utilized in a loading unit 100, e.g., a single use loading unit ("SULU") or a disposable loading unit ("DLU"). For simplicity, hereinafter, SULU or DLU will be referred to as "DLU," but it should be understood to include either or both a DLU or SULU. An exemplary example of this type of surgical stapling instrument is disclosed in U.S. Pat. No. 7,128,253, the entire disclosure of which is incorporated by reference herein.

Surgical stapling apparatus 10 generally includes a handle assembly 12 and an elongate body 14 extending distally from handle assembly 12. A DLU 100 is releasably secured to the distal end of elongate body 14. DLU 100 includes a cartridge assembly 200 housing a plurality of surgical fasteners or staples 223 (see FIG. 2) and an anvil assembly 300 movably secured in relation to cartridge assembly 200. Handle assembly 12 includes a stationary handle member 22, a movable handle member 24, and a barrel portion 26. An articulation lever 30 is mounted on the forward end of barrel portion 26 adjacent rotatable member 28 to facilitate articulation of DLU 100. A pair of knobs 32 are movably positioned along barrel portion 26. Knobs 32 are advanced distally to approximate or close cartridge and/or anvil assembly 200, 300, and retracted proximally to unapproximate or open cartridge and/or anvil assembly 200, 300. Actuation of movable handle member 24 applies lines of staples 223 to tissue. In order to properly orient cartridge and anvil assembly 200, 300 relative to the tissue to be stapled, surgical stapling apparatus 10 is additionally provided with a rotatable member 28 on the forward end of barrel portion 26. Rotation of rotatable member 28 relative to handle assembly 12 rotates elongate body 14 and loading unit 100 relative to handle assembly 12 so as to properly orient cartridge assembly 200 and anvil assembly 300 relative to the tissue to be stapled.

Figure 2:
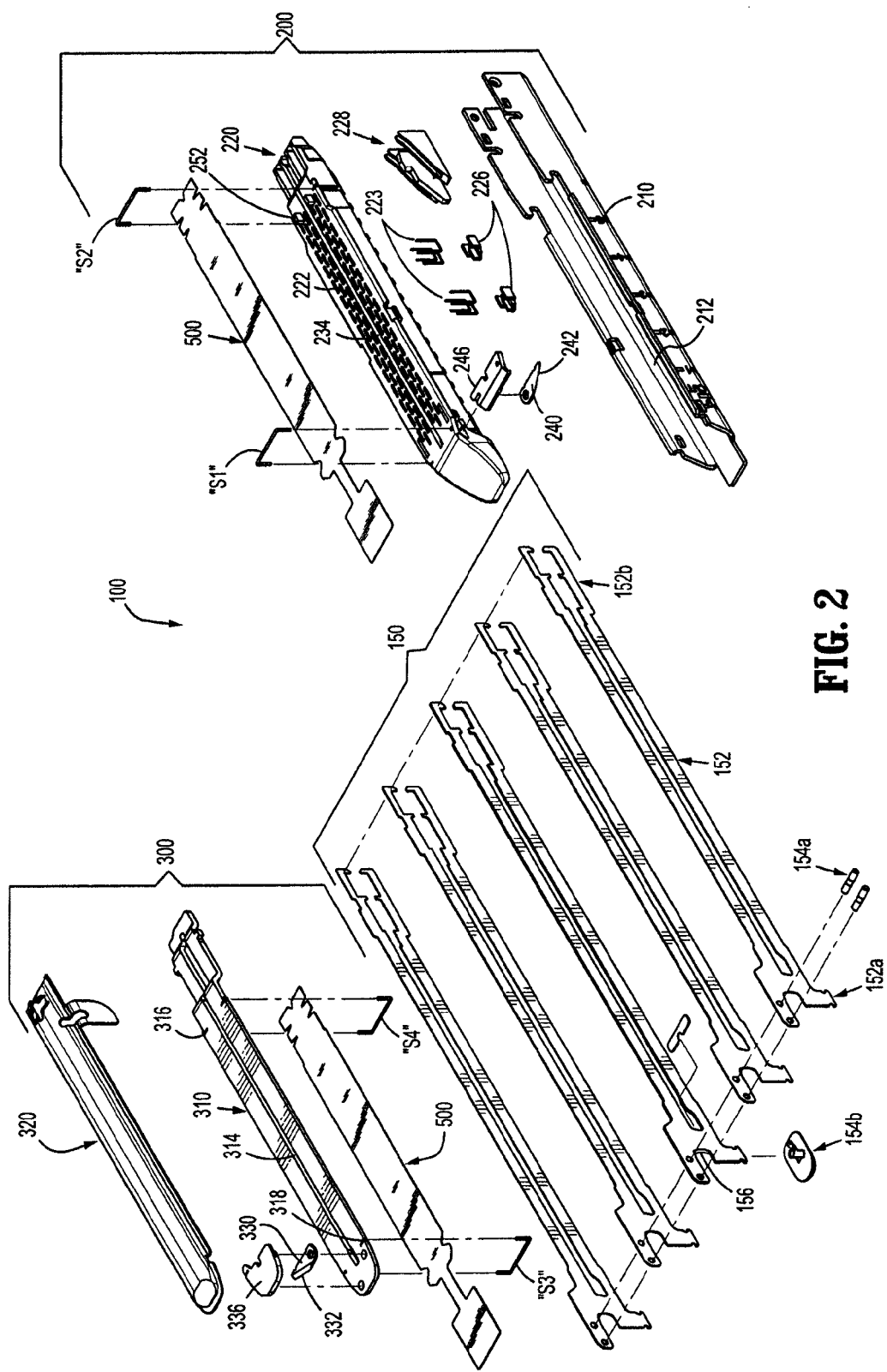
FIG. 2 is a top, exploded, perspective view of a distal end of a DLU of the surgical stapling apparatus of FIG. 1.

As seen in FIG. 2, cartridge assembly 200 includes a carrier 210 defining an elongated support channel 212. Elongated support channel 212 of carrier 210 is dimensioned and configured to selectively receive a staple cartridge 220 therein. Staple cartridge 220 includes retention slots 222 formed therein for receiving a plurality of fasteners 223 and pushers 226. A plurality of spaced apart longitudinal slots extend through staple cartridge 220 to accommodate upstanding cam wedges of actuation sled 228. A central longitudinal slot 234 is formed in and extends along the length of staple cartridge 220 to facilitate passage of knife blade 156 of drive bar 150 therethrough. During operation of surgical stapler 10, actuation sled 228 translates through staple cartridge 220 to advance the cam wedges into sequential contact with pushers 226, to cause pushers 226 to translate vertically within retention slots 222 and urge staples 223 from slots 222 into staple forming cavities of anvil plate 310 of anvil assembly 300.

Figure 10:
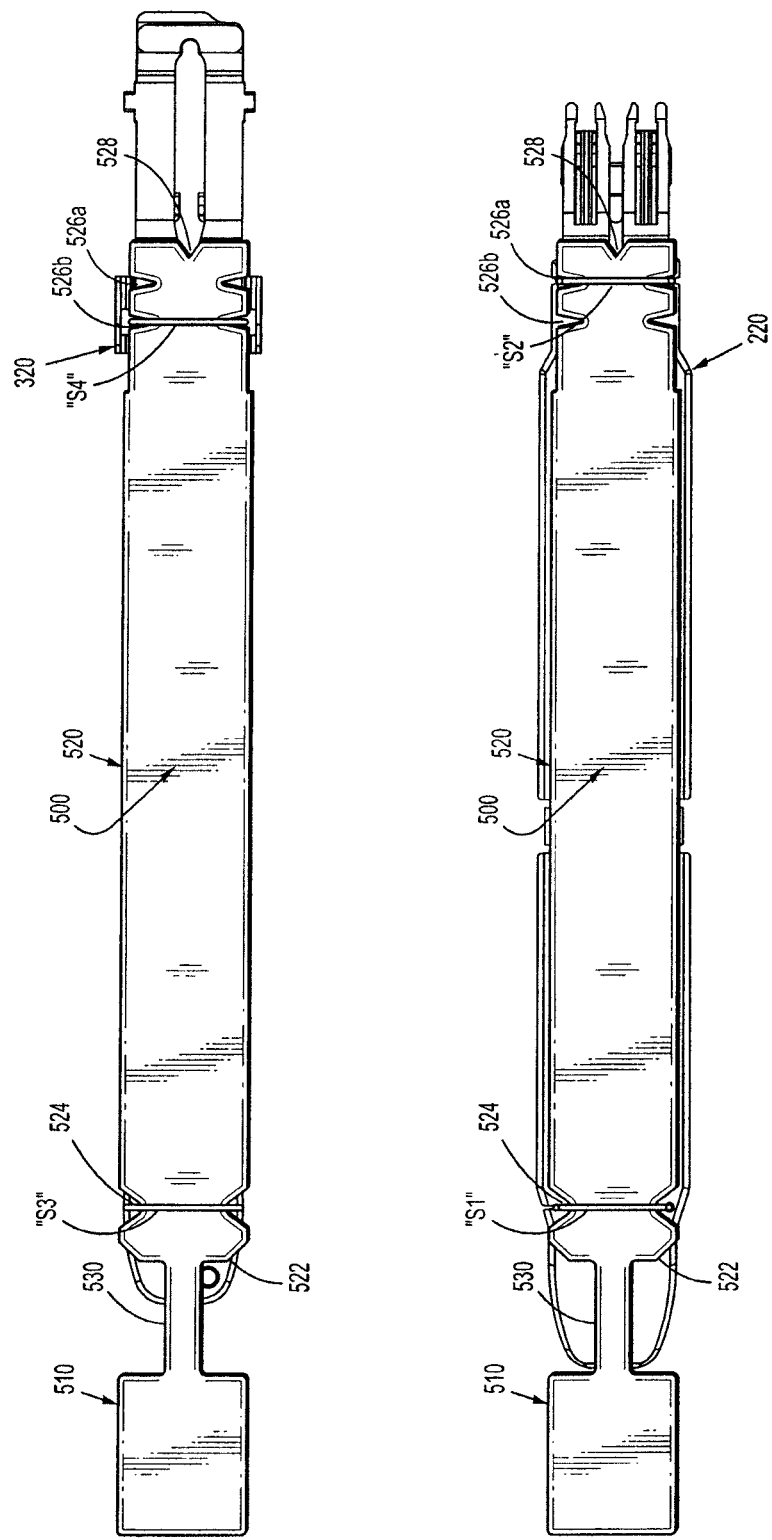
FIG. 10 is a plan view of the cartridge assembly of the DLU of FIGS. 4-8 and the anvil assembly of the DLU of FIG. 9, illustrating the attachment of the buttress of FIG. 3 at different attachment points of a respective cartridge assembly and anvil assembly.

As seen in FIG. 2, cartridge assembly 200 includes a surgical cartridge buttress 500 operatively secured to an upper surface of staple cartridge 220, by sutures "S1, S2," to overlie at least some of retention slots 222 and/or at least a portion of a length of longitudinal slot 234. A first suture "S1" is threaded through each of a distal pair of recesses or attachment points 238 and around/over distal portion of cartridge buttress 500 and, and a second suture "S2" is threaded through each of a proximal pair of recesses or attachment points 236 and around/over proximal portion of cartridge buttress 500. A first end of each suture "S1, S2" may be anchored or fixed in a respective one recesses of the proximal and distal pair of recesses or attachment points 236, 238 while a second end of each suture "S1, S2" passes transversely across respective distal and proximal portions of cartridge buttress 500 and is anchored or fixed in a respective other recess of the proximal and distal pair of recesses or attachment points 236, 238. As seen in FIG. 10, cartridge assembly 200 defines an axial distance "D1" between the distal pair of recesses or attachment points 238 and the proximal pair of recesses or attachment points 236.

Figure 9:
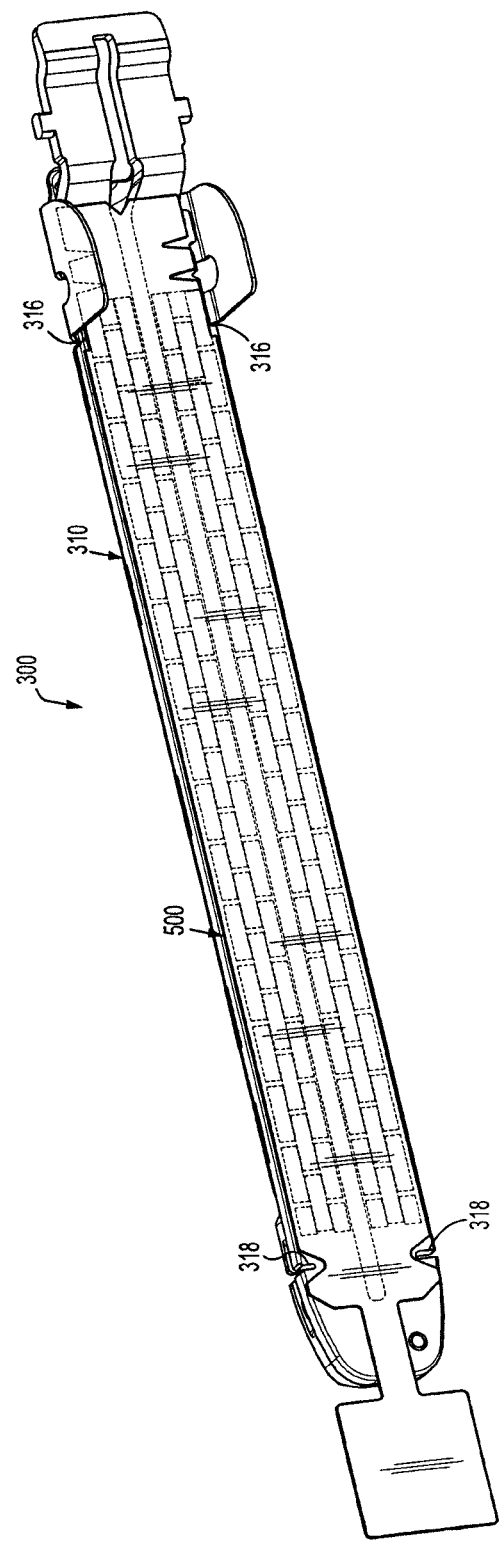
FIG. 9 is a perspective view of an anvil assembly of the DLU of FIG. 2, illustrating the buttress of FIG. 3 secured thereto.

With reference still to FIG. 2, anvil assembly 300 includes an anvil plate 310 having a plurality of staple deforming pockets/cavities 310a (see FIG. 9) and a cover plate 320 secured to a top surface of anvil plate 310. Anvil assembly 300 further includes a knife blade 330 operatively interposed within the cavity defined between anvil plate 310 and cover plate 320.

Anvil plate 310 defines a proximal pair of recesses or attachment points 316 formed near a proximal end of anvil plate 310 and disposed, one each, on opposed sides of longitudinal slot 314. Anvil plate 310 defines a distal pair of recesses or attachment points 318 formed near a distal end of anvil plate 310 and disposed, one each, on opposed sides of longitudinal slot 314. At least one recess of each of the proximal pair of recesses or attachment points 316 and the distal pair of recesses or attachment points 318 is in the form of a slot or notch having a constricting profile so as to frictionally engage and/or pinch a suture "S". Anvil assembly 300 further includes a surgical anvil buttress 500 operatively secured to a lower surface of anvil plate 310, by sutures "S3, S4," to overlie at least some of anvil pockets 310a and/or at least a portion of a length of longitudinal slot 314.

With reference still to FIG. 2, anvil buttress 500 is secured to a lower surface of anvil plate 310, by anchors "S3, S4", to overlie at least some of the anvil pockets and/or at least a portion of a length of longitudinal slot 314. In particular, an anchor "S3" is threaded across a distal portion of the anvil buttress 500 and each of the corresponding distal pair of recesses or attachment points 318, and an anchor "S4" is threaded across a proximal portion of anvil buttress 500 and each of the corresponding proximal pair of recesses or attachment points 316. As seen in FIG. 10, anvil assembly 300 defines an axial distance "D2" between the distal pair of recesses or attachment points 318 and the proximal pair of recesses or attachment points 316.

Reference may be made to U.S. patent application Ser. No. 12/342,400, filed on Dec. 23, 2008, the entire content of which is incorporated herein by reference, for a detailed discussion of the construction and operation of surgical stapling apparatus 10, cartridge assembly 200 and/or anvil assembly 300.

Buttress 500 for each of cartridge assembly 200 and anvil assembly 300 is provided to reinforce and seal staple lines applied to tissue by surgical stapling apparatus 10. Cartridge assembly 200 and anvil assembly 300 are particularly configured to allow surgical buttresses 500 to be localized on inwardly facing surfaces of cartridge assembly 200 and anvil assembly 300 in order to facilitate passage of surgical stapling apparatus 10 into the body of a patient without risk of tearing or wrinkling of the respective buttresses as surgical stapling apparatus 10 is inserted into and manipulated within the body of a patient. The material from which the buttress 500 is formed may be bioabsorbable or non-bioabsorbable. It should be understood that any combination of natural, synthetic, bioabsorbable and non-bioabsorbable materials may be used to form the buttress material. The buttress material may be porous or non-porous, combination of porous and non-porous layers. The non-porous buttress material may be utilized to retard or prevent tissue ingrowth from surrounding tissues thereby acting as an adhesion barrier and preventing the formation of unwanted scar tissue.

Additional exemplary materials for surgical buttresses 500 for use with the surgical stapling devices disclosed herein are set forth in commonly assigned U.S. Pat. Nos. 5,542,594; 5,908,427; 5,964,774; and 6,045,560, and commonly assigned U.S. Application Publication Nos. 2006/0085034, filed on Apr. 20, 2006; and 2006/0135992, filed on Jun. 22, 2006, the entire contents of each of which is incorporated herein by reference.

In an embodiment, surgical buttresses 500 may be fabricated from a suitable biocompatible and bioabsorbable material. Surgical buttresses 500 may also be fabricated from a non-absorbent material which does not retain fluid, for example, surgical buttresses 500 may be fabricated from "BIOSYN™" (a synthetic polyester, commercially available from Tyco Healthcare Group, LP d/b/a COVIDIEN, North Haven, Conn.), which is made from "GLYCOMER 631" (a block copolymer) which is a synthetic polyester composed of glycolide, dioxanone and trimethylene carbonate.

One block of the resulting copolymer contains randomly combined units derived from p-dioxanone (1,4-dioxan-2-one) and trimethylene carbonate (1,3-dioxan-2-one). A second block of the copolymer contains randomly combined units derived from glycolide and p-dioxanone. The resulting polyester is an ABA triblock terpolymer possessing about 60% glycolide, about 14% dioxanone, and about 26% trimethylene carbonate.

Anvil buttress and/or cartridge buttress 500 may be pre-loaded (i.e., from the manufacturer) onto anvil assembly 300 or cartridge assembly 200. Additional or replacement buttresses 500 for anvil assembly 300 and/or cartridge assembly 200 may be secured to either anvil assembly 300 or cartridge assembly 200 as needed or desired.

In operation, with DLU 100 coupled to a distal end of elongated body 14 of surgical stapling apparatus 10, and with anvil and cartridge buttresses 500 pre-loaded onto anvil assembly 300 and cartridge assembly 200, respectively, surgical stapling apparatus 10 is used in accordance with methods known by those skilled in the art. Once anvil assembly 300 and cartridge assembly 200 are clamped onto tissue, surgical stapling apparatus 10 is fired. In firing surgical stapling apparatus 10, drive bar 150 is advanced from a proximal-most position to a distal-most position of DLU 100. In so doing, knife blade 156 of drive bar 150 enters notch 528 of buttress 500 thereby facilitating the dividing of buttress 500 and reducing any incidents of pushing or bunching-up of buttress 500 by blade 156. As drive bar 150 begins to travel distally, knife blade 156 substantially simultaneously cuts through a central section of the proximal anchors "S2, S4" of anvil assembly 300 and cartridge assembly 200, thereby respectively freeing the proximal ends of anvil and cartridge buttresses 500 therefrom. As knife blade 156 is moved distally, knife blade 156 slices or cuts longitudinally through both anvil buttress 500 and cartridge buttress 500, thereby dividing the buttresses 500 substantially in half.

Additionally, as drive bar 150 approaches the distal-most position, drive bar 150 and/or knife blade 156 engage a suture cutting assembly or suture release assembly, as described in U.S. patent application Ser. No. 12/342,400, filed on Dec. 23, 2008, the entire content of which is incorporated herein by reference, to thereby sever or release distal sutures "S1 or S3" and thus release a distal end of buttress 500.

Figure 3:
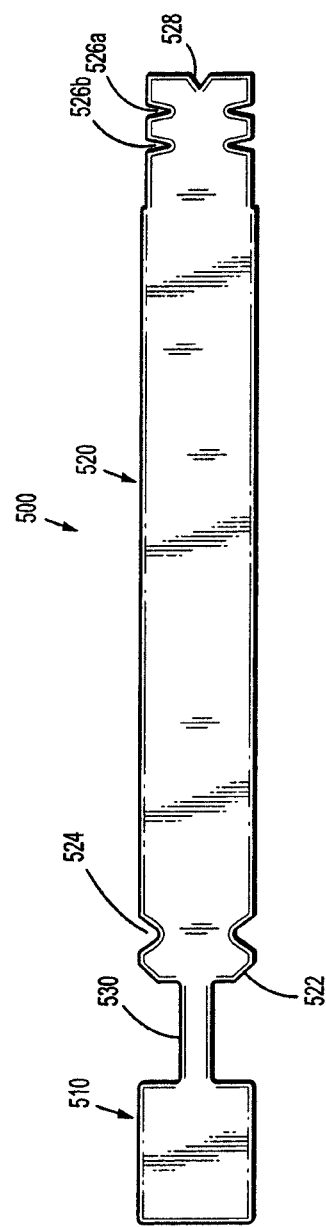
FIG. 3 is a top plan view of a buttress according to an embodiment of the present disclosure.
Figure 4:
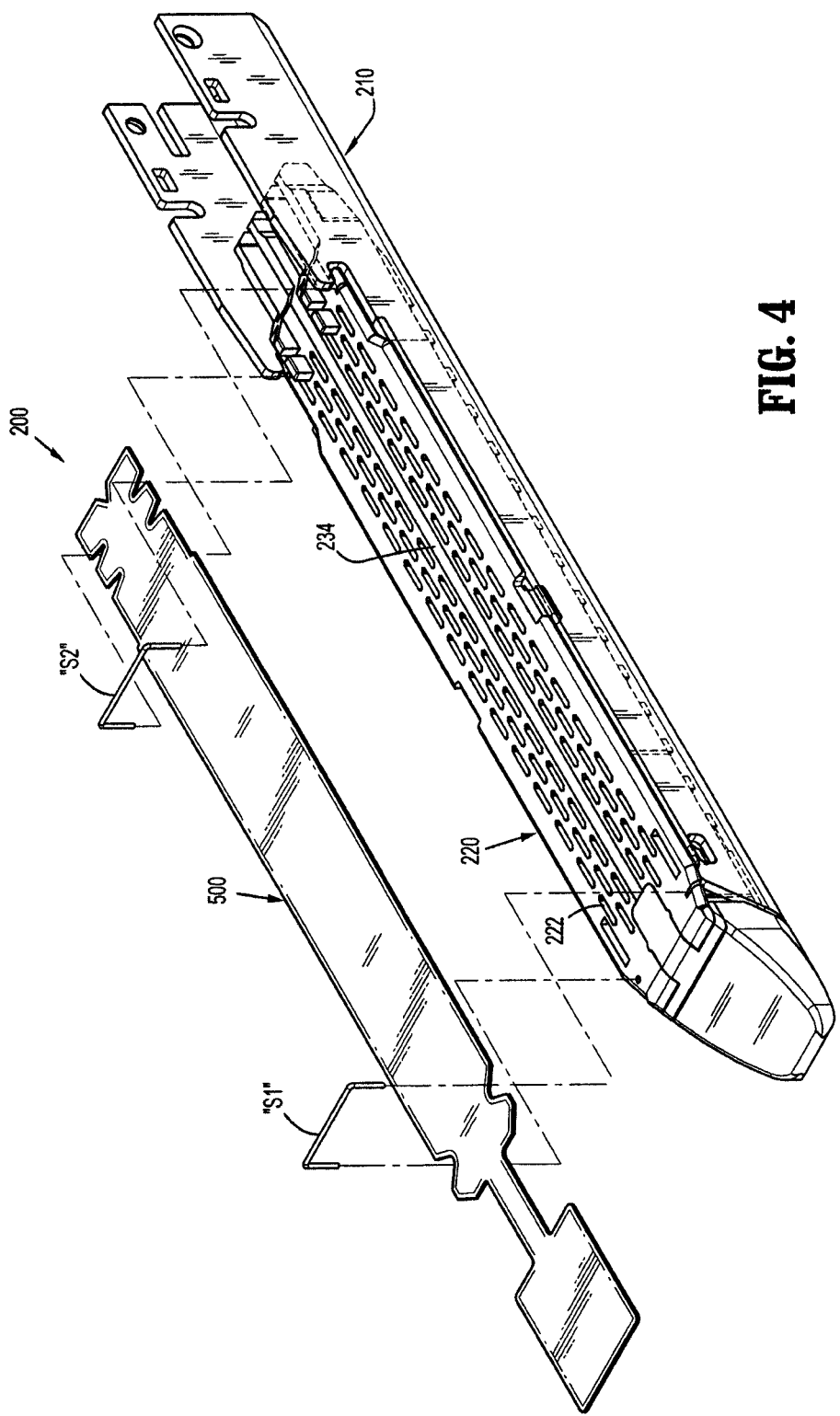
FIG. 4 is a top, perspective view of a cartridge half-section of the DLU of FIG. 2.
Figure 5:
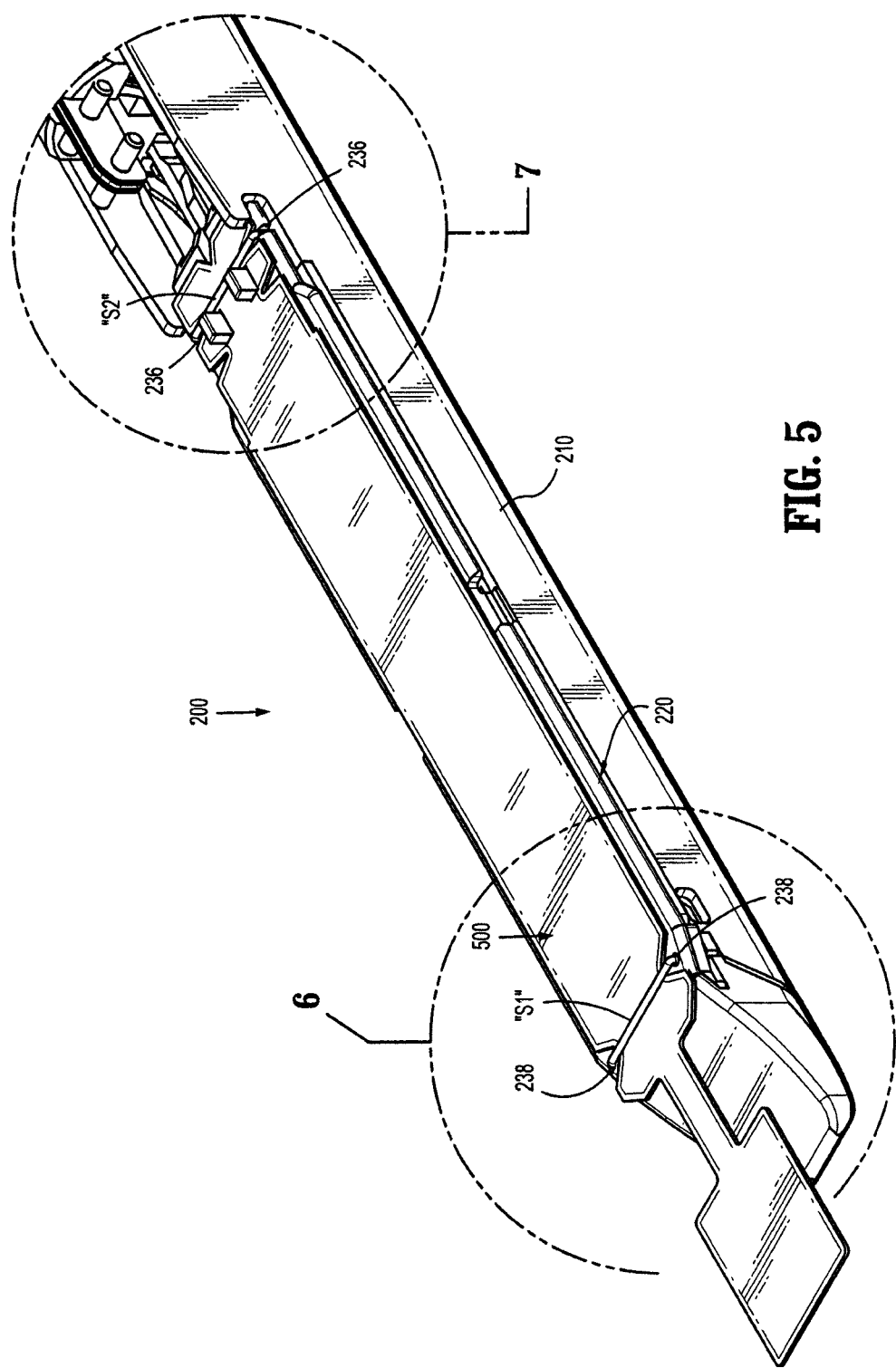
FIG. 5 is a perspective view of a cartridge assembly of the DLU of FIG. 2.
Figure 6:
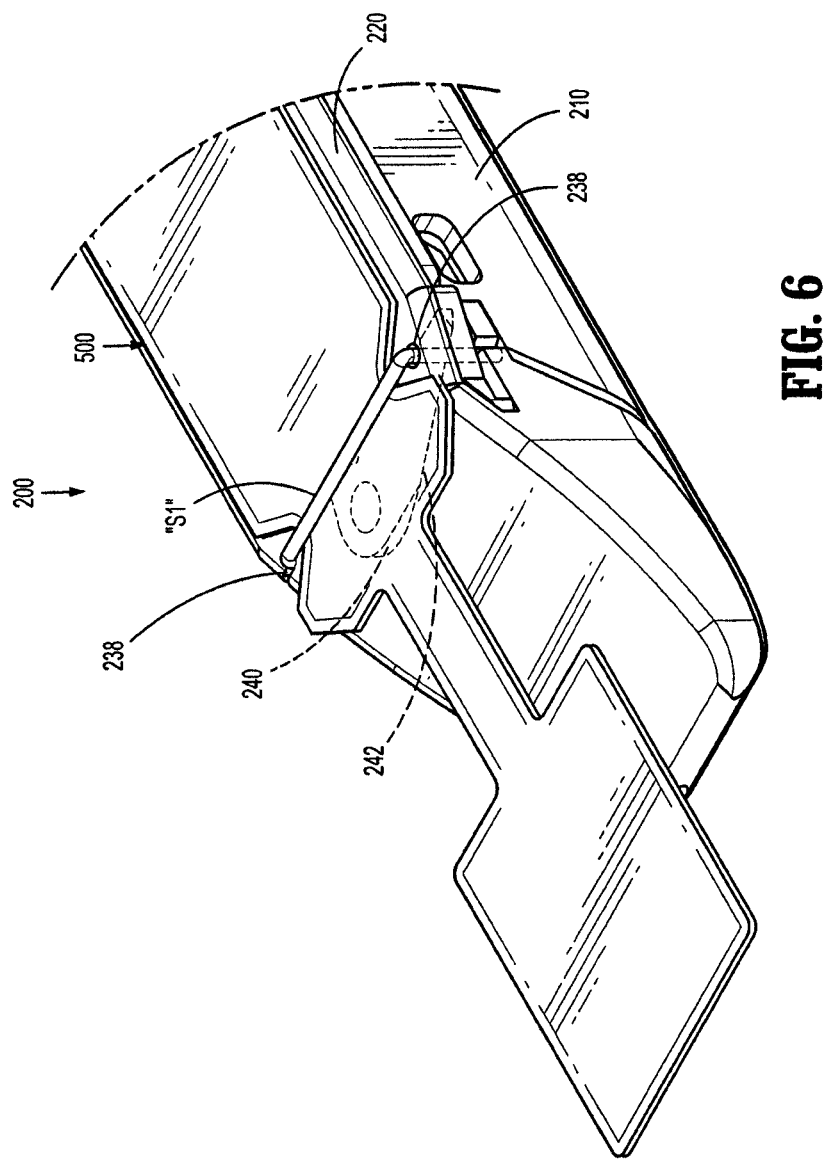
FIG. 6 is an enlarged perspective view of a distal end of the cartridge assembly of FIG. 5.
Figure 7:
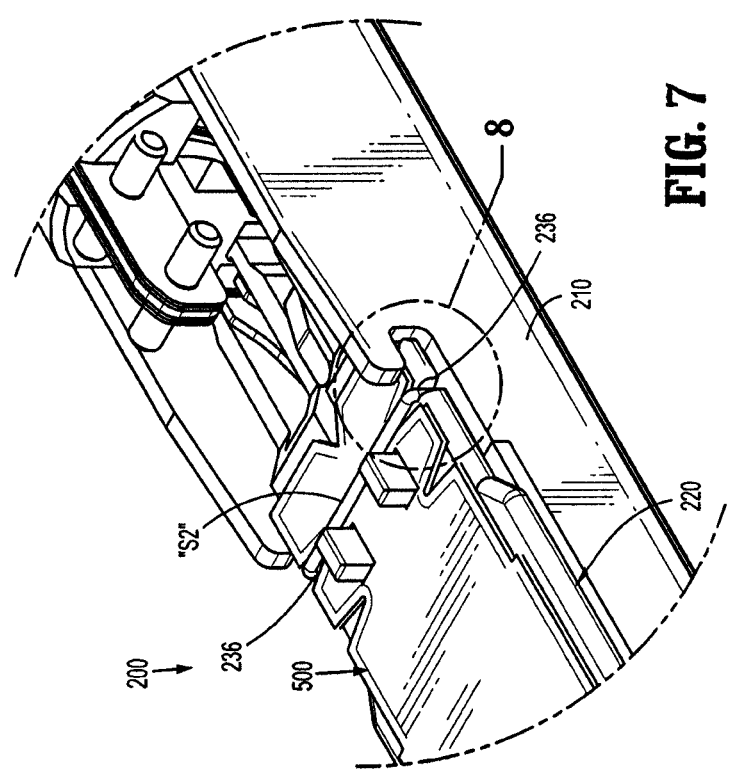
FIG. 7 is an enlarged view of the indicated area of detail of FIG. 5.
Figure 8:
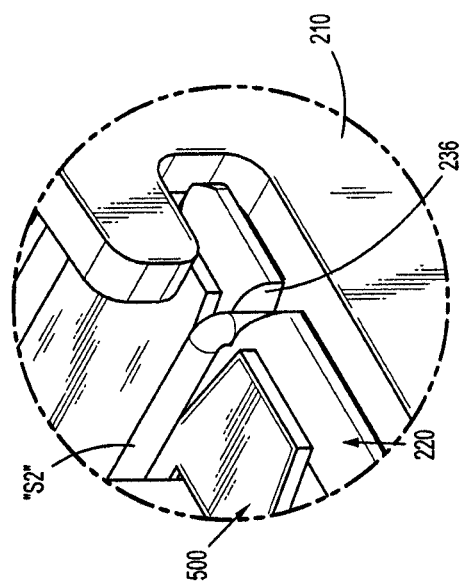
FIG. 8 is an enlarged view of the indicated area of detail of FIG. 7.

With reference to FIG. 3, an embodiment of a surgical buttress 500 having a uniform profile in accordance with the present disclosure, is illustrated. Buttress 500 includes a head portion 510, a body portion 520, and a neck portion 530 interconnecting head portion 510 and body portion 520.

Buttress 500 is configured to be detachably secured to any sized anvil assembly 300 and/or cartridge assembly 200, as described above. Body portion 520 of buttress 500 defines a pair of opposing distal recesses 524 on transverse edges near a distal location 522 thereof. The pair of opposing distal recesses 524 may be utilized to secure body portion 520 to a distal end of anvil assembly 300 and/or cartridge assembly 200, either through a use of suture "S1 or S3" or any other type of fastener, e.g., staple. Distal portion 522 of body portion 520 has a reduced transverse cross-sectional dimension, e.g., angled, arcuated, so as to be suitable for various types of anvil and cartridge assemblies having different shapes.

Body portion 520 of buttress 500 further defines two pairs of opposing proximal recesses 526a, 526b formed near a proximal end thereof. Each of the pair of proximal recesses 526a, 526b is disposed on a transverse side of body portion 520 near the proximal edge thereof. Such proximal recesses 526a, 526b serve to detachably secure buttress 500 to a proximal end of anvil assembly 300 and/or cartridge assembly 200. In order to accommodate various types of profiles, body portion 520 of buttress 500 preferably has been provided with two pairs of opposing recesses, a first proximal pair 526a, and a second proximal pair 526b (located distal of the first proximal pair 526a). Each of the proximal pair of recesses 526a, 526b has a substantially v-shape profile, although other shapes are contemplated.

In particular, when buttress 500 is to be used with a relatively longer anvil assembly 300 and/or cartridge assembly 200, then a suture "S2 or S4" is extended across a proximal end of body portion 520 of buttress 500, passed through the proximal-most pair of recesses 526a of buttress 500, and secured to respective recesses 316 of anvil assembly 300 and/or recesses 236 of cartridge assembly 200. Moreover, when buttress 500 is to be used with a relatively shorter anvil assembly 300 and/or cartridge assembly 200, then a suture "S2 or S4" is extended across a proximal end of body portion 520 of buttress 500, passed through the distal pair 526b of the proximal pair of recesses of buttress 500, and secured to respective recess 316 of anvil assembly 300 and/or recesses 236 of cartridge assembly 200.

According to another aspect of the present disclosure, a single profile or configuration buttress 500 may be used in connection with cartridge assembly 200 and/or anvil assembly 300. For example, the buttresses 500 that are used in connection with cartridge assembly 200 and anvil assembly 300 each may have the same overall length, width, thickness, perimetrical profile and material of construction.

In particular, as seen in FIG. 10, when buttress 500 is used in connection with cartridge assembly 200, a suture "S1" may extend transversely across a distal end portion of cartridge assembly 200 and be captured by or otherwise be secured to distal pair of recesses or attachment points 238 of cartridge assembly 200, wherein suture "S1" is in registration with distal recesses 524 of secure body portion 520 of buttress 500. Additionally, when buttress 500 is used in connection with cartridge assembly 200, a suture "S2" may extend transversely across a proximal end portion of cartridge assembly 200 and be captured by or otherwise secured to each of a proximal pair of recesses or attachment points 236 of cartridge assembly 200, wherein suture "S2" is in registration with the proximal-most pair 526a of the proximal pair of recesses of body portion 520 of buttress 500.

With continued reference to FIG. 10, when buttress 500 is used in connection with anvil assembly 300, a suture "S3"

may extend transversely across a distal end portion of anvil assembly 300 and be captured by or otherwise secured to the distal pair of recesses or attachment points 318 of anvil assembly 300, wherein suture "S3" is in registration with distal recesses 524 of secure body portion 520 of buttress 500. Additionally, when buttress 500 is used in connection with anvil assembly 300, a suture "S4" may extend transversely across a proximal end portion of anvil assembly 300 and be captured by or otherwise secured to each of a proximal pair of recesses or attachment points 316 of anvil assembly 300, wherein suture "S4" is in registration with the distal pair 526*b* of the proximal pair of recesses of body portion 520 of buttress 500.

Neck portion 530 connects head portion 510 to a distal end of body portion 520. Generally, head portion 510 is in a substantially rectangular shape which is used as a tab to facilitate placement of buttress 500 in position on anvil assembly 300 and/or cartridge assembly 200. Following placement of buttress 500 on anvil assembly 300 and/or cartridge assembly 200, head portion 510 and neck portion 530 may be torn or otherwise cut away from body portion 520. The neck portion may have perforations for this purpose, in certain embodiments.

Body portion 520 further includes a notch 528 at a proximal edge thereof. Notch 528 is substantially centered with respect to the longitudinal axis. Notch 528 which has a triangular or V-shape configuration (although other shapes are contemplated) may be utilized to provide a lead-in for the knife during a cutting of surgical cartridge buttress 500.

The uniform profile of buttress 500 which simultaneously satisfies the requirements of one or more different assemblies offers advantages of simplifying the assembly process, minimizing the total number of unique components, and reducing assembly costs associated therewith.

Moreover, buttress 500 may be used on or in connection with cartridge assembly 200 and/or anvil assembly 300. In this manner, a single profile buttress 500 is produced and used for cartridge assembly 200 and/or anvil assembly 300. As such, the manufacturing and storage costs for buttresses 500 may be reduced.

As mentioned above, DLU 100 includes an anvil surgical buttress 500 and a cartridge surgical buttress 500 pre-loaded onto anvil assembly 300 and cartridge assembly 200. An exemplary method of loading anvil assembly 300 and/or cartridge assembly 200 with a buttress 500 will now be described.

During the manufacturing and/or assembly process of DLU 100, loading of anvil assembly 300 and/or cartridge assembly 200 with buttress 500 includes placing a buttress 500 atop a tissue contacting surface of anvil assembly 300 and/or cartridge assembly 200 such that notch 528 of buttress is disposed near a proximal end of anvil assembly 300 and/or cartridge assembly 200 and head portion 510 of buttress 500 extends from a distal end of anvil assembly 300 and/or cartridge assembly 200. With buttress 500 so positioned against anvil assembly 300 and/or cartridge assembly 200, proximal sutures "S2" and/or "S4" are pulled down. Tension is then applied to buttress 500, in a distal direction, by pulling on head portion 510. Distal sutures "S1" and/or "S3" are then pulled down. At this time, all the sutures "S1-S4" are cinched in the respective attachment points 316, 318, 236, 238 of anvil assembly 300 and/or cartridge assembly 200. Following cinching of sutures "S1-S4," head portion 510 of buttress 500 may be released. Next, DLU 100 may be removed from a nesting and head portion 510 and neck portion 530 of buttress 500 may be removed or severed from body portion 520.

The present disclosure also contemplates a method of forming the buttress. The buttress is formed from a suitable biocompatible or biocompatible and bioabsorbable material. In certain preferred embodiments, the buttresses are each fabricated from a non-absorbent material which does not retain fluid. The buttresses, in certain embodiments, are each fabricated from "BIOSYN" made from GLYCOMER 631 (a block copolymer), a synthetic polyester composed of glycolide, dioxanone and trimethylene carbonate.

One block of the resulting copolymer contains randomly combined units derived from p-dioxanone (1,4-dioxan-2-one) and trimethylene carbonate (1,3-dioxan-2-one). The second block of the copolymer contains randomly combined units derived from glycolide and p-dioxanone. The resulting polyester is an ABA triblock terpolymer possessing about 60% glycolide, about 14% dioxanone, and about 26% trimethylene carbonate.

Exemplary surgical buttresses "B" for use with the surgical stapling devices disclosed herein are shown and described in commonly assigned U.S. Pat. Nos. 5,542,594; 5,908,427; 5,964,774; and 6,045,560, and commonly assigned U.S. Application Serial Nos. 2006/0085034, filed on Apr. 20, 2006; and 2006/0135992, filed on Jun. 22, 2006, the entire contents of each of which is incorporated herein by reference.

The shape of the buttress may be formed by forming a sheet of the biocompatible material and cutting the desired shape into the sheet. The buttress may also be molded in the desired shape. In certain embodiments, a sheet of the biocompatible material is formed and then the profile or shape is cut off the sheet using roller die sets. A method of forming the buttress can follow these steps: a sheet of buttress material is fed through one side of a tool; the tool has the roller die sets with the exact desired profiles on it; the die sets stamp the exact profile on the sheet of buttress material; the profile is still loosely connected to the sheet of buttress material so that the sheet of buttress material comes out of the tool from a second side. The buttresses with the desired profiles are then pulled off the sheet of buttress material, which can be done manually.

While the above-described embodiments surgical staplers incorporating the use of movable knife blades to sever and release surgical buttresses from the tissue contacting surfaces of the anvil assembly and the cartridge assembly have been shown and described in relation to endoscopic surgical staplers, it is envisioned and within the scope of the present disclosure that any of the above-embodiments may be incorporated into any type of surgical stapler, including and not limited to open surgical staplers, such as, for example, linear surgical staplers and transverse surgical staplers.

Moreover, while only distal and proximal sutures have been shown and described as securing buttress 500 to anvil assembly 300 and/or cartridge assembly 300, it is contemplated that any number of transverse sutures may be provided along a length of the anvil assembly and/or cartridge assembly to aid with the securement of buttress 500 along a length thereof.

It will be understood that various modifications may be made to the embodiments disclosed herein. For example, the stapling apparatus need not apply staples but rather may apply two part fasteners as is known in the art. Further, the length of the linear row of staples or fasteners may be modified to meet the requirements of a particular surgical procedure. Thus, the length of a single stroke of the actuation shaft and/or the length of the linear row of staples and/or fasteners within a disposable loading unit may be varied accordingly. Therefore, the above description should not be construed as limiting, but merely as exemplifications of preferred embodiments. Those skilled in the art will envision other modifications within the scope and spirit of the claims appended thereto.

What is claimed is:

1. A surgical buttress for a surgical stapler having a staple cartridge assembly and an anvil assembly, the surgical buttress comprising a body portion configured to substantially overlie either the staple cartridge assembly or the anvil assembly, the surgical buttress defining a distal attachment feature, a first proximal attachment feature, and a second proximal attachment feature in at least one lateral edge of the body portion, at least one of the distal attachment feature, the first proximal attachment feature, or the second proximal attachment feature being at least one recess defined in the at least one lateral edge of the body portion, the first proximal attachment feature being offset an axial distance from the second proximal attachment feature, the first proximal attachment feature positioned for registering with a proximal attachment point of the staple cartridge assembly, and the second proximal attachment feature positioned for registering with a proximal attachment point of the anvil assembly.

2. The surgical buttress according to claim 1, wherein the first proximal attachment feature is the at least one recess defined in the at least one lateral edge of the body portion.

3. The surgical buttress according to claim 1, wherein the second proximal attachment feature is the at least one recess defined in the at least one lateral edge of the body portion.

4. The surgical buttress according to claim 1, wherein the distal attachment feature is the at least one recess defined in the at least one lateral edge of the body portion.

5. The surgical buttress according to claim 1, wherein the body portion is fabricated from a biocompatible and bioabsorbable material.

6. The surgical buttress according to claim 1, wherein the body portion defines a recess formed in a proximal edge thereof.

7. The surgical buttress according to claim 6, wherein the recess is a notch having a v-shape profile.

8. The surgical buttress according to claim 1, wherein at least one of the distal attachment feature, the first proximal attachment feature, or the second proximal attachment feature is a pair of recesses defined in opposed lateral edges of the body portion.

9. The surgical buttress according to claim 1, further comprising a head portion and a neck portion.

10. A surgical buttress for a surgical stapler having a staple cartridge assembly and an anvil assembly, the surgical buttress comprising a body portion configured to substantially overlie either the staple cartridge assembly or the anvil assembly, the surgical buttress defining first and second proximal attachment features in at least one lateral edge of the body portion, at least one of the first or second proximal attachment features being at least one recess defined in the at least one lateral edge of the body portion, the first and second proximal attachment features being configured for registration with the staple cartridge assembly or the anvil assembly.

11. The surgical buttress according to claim 10, wherein the first proximal attachment feature is the at least one recess defined in the at least one lateral edge of the body portion.

12. The surgical buttress according to claim 10, wherein the second proximal attachment feature is the at least one recess defined in the at least one lateral edge of the body portion.

13. The surgical buttress according to claim 10, further comprising a distal attachment feature that is at least one recess defined in the at least one lateral edge of the body portion.

14. The surgical buttress according to claim 10, wherein the body portion is fabricated from a biocompatible and bioabsorbable material.

15. The surgical buttress according to claim 10, wherein the body portion of the surgical buttress defines a recess formed in a proximal edge thereof.

16. The surgical buttress according to claim 15, wherein the recess is a notch having a v-shape profile.

17. The surgical buttress according to claim 10, wherein at least one of the first proximal attachment feature or the second proximal attachment feature includes a pair of recesses defined in opposed lateral edges of the body portion.

18. The surgical buttress according to claim 10, further comprising a head portion and a neck portion.

* * * * *

UNITED STATES PATENT AND TRADEMARK OFFICE
CERTIFICATE OF CORRECTION

PATENT NO.       : 9,622,745 B2                                            Page 1 of 1
APPLICATION NO. : 14/047386
DATED            : April 18, 2017
INVENTOR(S)      : Ingmanson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 670 days.

Signed and Sealed this
Twenty-fifth Day of September, 2018

Andrei Iancu
*Director of the United States Patent and Trademark Office*